United States Patent
Dengler et al.

(10) Patent No.: US 10,500,024 B2
(45) Date of Patent: Dec. 10, 2019

(54) BRUSH HEAD ASSEMBLY AND METHODS OF MANUFACTURE

(71) Applicant: KONINKLIJKE PHILIPS N.V., Eindhoven (NL)

(72) Inventors: Evan Dak Wah Dengler, Seattle, WA (US); Bart Johannes Massee, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 65 days.

(21) Appl. No.: 15/573,293

(22) PCT Filed: May 11, 2016

(86) PCT No.: PCT/IB2016/052695
§ 371 (c)(1),
(2) Date: Nov. 10, 2017

(87) PCT Pub. No.: WO2016/181322
PCT Pub. Date: Nov. 17, 2016

(65) Prior Publication Data
US 2018/0132988 A1 May 17, 2018

Related U.S. Application Data

(60) Provisional application No. 62/161,361, filed on May 14, 2015.

(51) Int. Cl.
*A46D 3/00* (2006.01)
*A61C 17/22* (2006.01)
(Continued)

(52) U.S. Cl.
CPC .............. *A61C 17/222* (2013.01); *A46B 3/04* (2013.01); *A46B 3/06* (2013.01); *A46B 3/20* (2013.01);
(Continued)

(58) Field of Classification Search
CPC .... A46B 3/04; A46B 3/20; A46B 9/04; A46D 3/00
See application file for complete search history.

(56) References Cited

U.S. PATENT DOCUMENTS

| 2,271,835 A | * | 2/1942 | Cave | ........................ A46D 3/05 |
| | | | | 15/199 |
| 5,474,366 A | | 12/1995 | Zahoransky et al. | |

(Continued)

FOREIGN PATENT DOCUMENTS

| CN | 1547442 A | 11/2004 |
| EP | 1593321 A1 | 11/2005 |

(Continued)

*Primary Examiner* — Michael D Jennings

(57) ABSTRACT

A brush head (32) including: a supporting portion (42) of a brush neck (40); a plurality of bristle tufts (21), each of which comprises a plurality of bristle strands having a proximal end (23) and a free end (25), wherein each of the plurality of bristle tufts comprises a proximal end head portion (26) melted into a first shape within a mold; and an elastomeric matrix (30) comprising at least a portion of the hard brush neck and the proximal end head portions, wherein the first shape of the proximal end head portion is configured to engage the elastomeric matrix such that the bristle tufts are retained within the elastomeric matrix.

7 Claims, 8 Drawing Sheets

(51) Int. Cl.

| | | |
|---|---|---|
| *A46B 3/06* | (2006.01) | |
| *A46B 3/20* | (2006.01) | |
| *A46D 3/04* | (2006.01) | |
| *A46B 3/04* | (2006.01) | |
| *A46B 9/04* | (2006.01) | |
| *B29C 45/14* | (2006.01) | |
| *B29K 21/00* | (2006.01) | |
| *B29K 677/00* | (2006.01) | |
| *B29L 31/42* | (2006.01) | |

(52) U.S. Cl.
CPC ............... *A46B 9/04* (2013.01); *A46D 3/005* (2013.01); *A46D 3/045* (2013.01); *B29C 45/14385* (2013.01); *B29C 2045/14868* (2013.01); *B29K 2021/003* (2013.01); *B29K 2677/00* (2013.01); *B29L 2031/425* (2013.01)

(56) References Cited

U.S. PATENT DOCUMENTS

| | | |
|---|---|---|
| 5,802,656 A | 9/1998 | Dawson et al. |
| 5,970,564 A | 10/1999 | Inns et al. |
| 6,088,870 A | 7/2000 | Holbein |
| 6,406,099 B2 | 6/2002 | Boucherie |
| 7,281,768 B2 | 10/2007 | Sato et al. |
| 7,600,288 B1 | 10/2009 | Givonetti |
| 7,992,247 B2 | 8/2011 | Pfenniger et al. |
| 8,069,524 B2 | 12/2011 | Kraemer |
| 8,099,819 B2 | 1/2012 | Kraemer |
| 2001/0024060 A1 | 9/2001 | Boucherie |
| 2001/0038237 A1 | 11/2001 | Boucherie |
| 2002/0132572 A1* | 9/2002 | Lageson ............... B24D 13/10 451/526 |
| 2003/0041402 A1* | 3/2003 | Stein ..................... A46D 3/005 15/167.1 |
| 2007/0006410 A1 | 1/2007 | Kraemer |
| 2007/0271717 A1 | 11/2007 | Clos |
| 2008/0168613 A1* | 7/2008 | Kraemer ................ A46B 9/12 15/167.1 |
| 2008/0315668 A1* | 12/2008 | Huber ................ B29C 45/0062 300/21 |
| 2011/0232016 A1* | 9/2011 | Yu .......................... A46B 3/005 15/176.6 |
| 2012/0233790 A1 | 9/2012 | Uchida et al. |
| 2013/0205529 A1* | 8/2013 | Flesch .................... A46B 3/02 15/190 |
| 2014/0232173 A1 | 8/2014 | Birk et al. |
| 2015/0115692 A1* | 4/2015 | Hiramoto ............... A46D 1/08 300/21 |
| 2015/0130259 A1* | 5/2015 | Birk ........................ A46D 1/08 300/19 |
| 2016/0166051 A1* | 6/2016 | Shokoohi ................ A46B 9/04 15/167.1 |

FOREIGN PATENT DOCUMENTS

| | | |
|---|---|---|
| EP | 2708155 A1 | 3/2014 |
| WO | 2004080238 A1 | 9/2004 |
| WO | 2006109077 A1 | 10/2006 |

\* cited by examiner

BRUSH HEAD ASSEMBLY AND METHODS OF MANUFACTURE

CROSS-REFERENCE TO PRIOR APPLICATIONS

This application is the U.S. National Phase application under 35 U.S.C. § 371 of International Application No. PCT/IB2016/052695, filed on May 11, 2016, which claims the benefit of U.S. Provisional Patent Application No. 62/161,361, filed on May 14, 2015. These applications are hereby incorporated by reference herein.

FIELD OF THE INVENTION

The present disclosure is directed generally to a brush head assembly with bristle tufts retained within an elastomeric matrix, as well as to methods for manufacturing the brush head assembly.

BACKGROUND

Periodontal diseases are thought to be infectious diseases caused by bacteria present in dental plaques. Tooth brushing is a highly effective method to remove dental plaque from the teeth. Power toothbrushes can enhance the removal of dental plaque. Such power toothbrushes have a set of bristles attached to a brush head which is moved by a driver that causes the bristles to scrub dental surfaces.

The brush heads of both manual and power toothbrushes comprise bristles which are used to clean the teeth, tongue, and cheeks. In some toothbrushes, the bristles are organized into bristle tufts contained within retention rings. The retention rings serve to secure the bristle tufts within the brush head and often have a hollow circular shape with an interior and exterior circular circumference. During manufacture, the bristle tufts are inserted into the hollow interior of the retention ring, and the bristles in the retention ring are then secured into a brush head material which is then cooled or allowed to cool in order to form the final brush head.

Often, however, the retention rings are not firmly secured within the brush head. As a result, the ring and bristle tuft can be or become loose within the brush head, and the bristles might not always be positioned at an angle optimal for brushing. As such, under the dynamic conditions of motion induced by the power toothbrush operation, for example, the bristle tuft structure can undergo higher stresses under the dynamic motion, which could lead to separation. Further, the process of organizing the bristles into tufts within the retention rings and then cooling the brush head material, or allowing it to cool, in order to fix the tufts in place can be time-consuming and expensive.

Accordingly, there is a need in the art for brush head assemblies, and methods of their manufacture, that permanently and efficiently retain bristle tufts within the brush head while ensuring flexibility of the bristles during use.

SUMMARY OF THE INVENTION

The present disclosure is directed to inventive methods for manufacturing a brush head with secured bristle tufts. Various embodiments and implementations herein are directed to manufacturing methods in which bristle tufts ends are melted to form proximal end tufts of varying shapes and sizes, which are then embedded within an elastomeric matrix resulting in a completed brush head. Using the various embodiments and implementations herein, cost-effective and efficient production of brush heads with secured bristle tufts is substantially improved. For example, in some embodiments, when a bristle tuft is pulled, some of the force is distributed to the surrounding elastomeric matrix due to the shape of the proximal end head portion of the bristle tufts. This provides for greater flexibility of tuft movement, and also, by reducing the pressure, reduces the probability of the retaining head breaking through the retaining ring, causing premature brush head failure due to bristle tuft loss.

Generally in one aspect, a brush head is provided. The brush head includes: a hard brush neck; a plurality of bristle tufts, each of which comprises a plurality of bristle strands having a proximal end and a free end, wherein each of the plurality of bristle tufts comprises a proximal end head portion melted into a first shape within a mold; and an elastomeric matrix comprising at least a portion of the hard brush neck and the proximal end head portions, wherein the first shape of the proximal end head portion is configured to engage the elastomeric matrix such that the bristle tufts are retained within the elastomeric matrix.

According to an embodiment, the proximal end head portions of two or more neighboring bristle tufts are interconnected.

According to an embodiment, the brush head further includes a plurality of retention rings, each of the plurality of retention rings configured to receive a respective one of the plurality of bristle tufts.

According to an embodiment, the proximal end head portions comprise a trapezoidal shape.

According to an embodiment, the proximal end head portions comprise a u-shape.

According to an aspect is a method for manufacturing a brush head. The method includes the steps of: positioning a proximal end of each of a plurality of bristle tufts into a mold, the mold comprising a plurality of cavities each configured to receive at least one of the plurality of bristle tufts; applying heat to each of the bristle tuft proximal ends at a temperature and distance sufficient to at least partially melt the bristle tuft proximal end to create a proximal end head portion, wherein each of the cavities is further configured to at least partially shape the proximal end head portion as it at least partially melts; removing at least a portion of the mold, wherein removing the mold exposes the proximal end head portion of the plurality of bristle tufts; and molding a thermoplastic elastomer to create an elastomeric matrix that at least partially encompasses the proximal head portions.

According to an embodiment, the method further includes the step of removing, after the molding step, a remaining portion of the mold.

According to an embodiment, the method further includes the step of positioning a brush neck in proximity to the proximal end head portions.

According to an embodiment, the mold further comprises one or more channels between at least some of the cavities, wherein the channels are configured to receive at least a portion of a melted bristle tuft during the applying step.

According to an embodiment, at least a portion of each of the cavities of the mold comprises a trapezoidal shape.

According to an embodiment, at least a portion of each of the cavities of the mold comprises u-shape.

According to an aspect a brush head assembly for a power toothbrush is provided. The brush head assembly includes a neck and a brush head, the brush head comprising: a hard brush neck; a plurality of bristle tufts, each of which comprises a plurality of bristle strands having a proximal end and a free end, wherein each of the plurality of bristle tufts comprises a proximal end head portion melted into a first shape within a mold; and an elastomeric matrix comprising at least a portion of the hard brush neck and the proximal end head portions, wherein the first shape of the proximal end head portion is configured to engage the elastomeric matrix such that the bristle tufts are retained within the elastomeric matrix.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a brush head assembly with bristle tufts retained within an elastomeric matrix, and methods of their manufacture. More generally, Applicants have recognized and appreciated that it would be beneficial to provide a brush head formed with bristle tufts that have a molded proximal end head portion, thereby increasing engagement with the elastomeric matrix and improving bristle retention which is beneficial to a brush head's function, especially in powered toothbrush devices. A particular goal of utilization of certain embodiments of the present disclosure is the ability to efficiently manufacture brush heads with improved retention of the bristle tuft and improved bristle tuft flexibility. In view of the foregoing, various embodiments and implementations are directed to a brush head assembly in which a bristle tuft is exposed to heat in order to shape the proximal end head portion of the bristle tuft and increase engagement with the elastomeric matrix.

The brush heads disclosed and described herein can be used with any manual or power toothbrush device. One example of a power toothbrush device that the brush head can be used with Sonicare® devices available from Koninklijke Philips Electronics N.V. This oral care device is based upon an actuator with a reciprocating brush head including bristles to provide an effective cleaning of a user's teeth.

Figure 1:
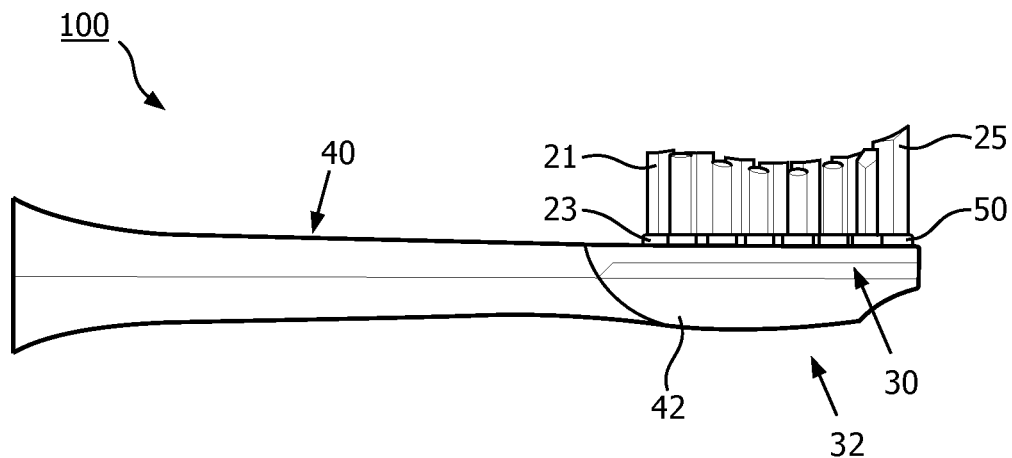
FIG. 1 is a schematic representation of a side view of a brush head assembly in accordance with an embodiment.

Referring to FIG. 1, in one embodiment, a schematic representation of a brush head assembly 100 is provided. The brush head assembly includes a neck 40, which can be coupled to any manual brush shaft, or, more preferably, to any actuator and drive shaft (not shown) made or suitable for oral care devices now known or to be developed. The brush head 32 of the brush head assembly includes a plurality of bristle tufts 21, each of which comprises a plurality of bristle strands. According to an embodiment, the bristle tufts are composed of nylon, or another suitable material, and optionally can be coated with polyurethane, polybutylene terephthalate (PBT), polyolefin, combinations of these, or a similar polymer. Each bristle tuft includes a proximal end 23 and a free end 25, where the proximal end of each bristle tuft is retained within the brush head assembly 100. Each bristle tuft 21 can be retained within a retention ring 50. The proximal end of the bristle tuft and the retention rings and the supporting portion of the neck 42 are retained within a flexible elastomeric matrix 30 to form a head portion 32 of the brush head assembly 100. According to an embodiment, the elastomeric matrix 30 is preferably made from a flexible thermoplastic elastomer (TPE), and the retention rings are preferably made from thermoplastic polymer such as polypropylene. Each of the neck 40, supporting portion of the neck 42, and the retention rings 50 is preferably made from a material with a higher elastic modulus value than the elastomeric matrix 30.

Figure 2:
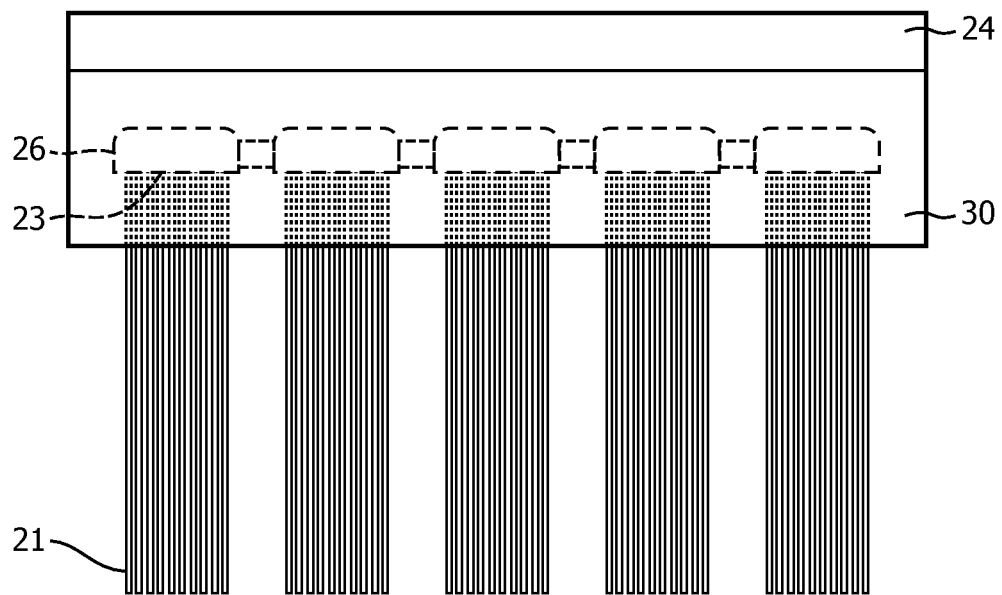
FIG. 2 is a schematic representation of a portion of a brush head assembly in accordance with an embodiment.

Referring to FIG. 2, in one embodiment, is a cut-away view of a portion of the brush head 32. Each of the bristle tufts 21 has a proximal end 23 with a proximal end head portion 26 which is embedded in the elastomeric matrix 30. According to an embodiment, the proximal end head portions 26 of neighboring bristle tufts are joined during manufacture to form a network of bristle tufts which provides better adherence of the bristle tufts within the elastomeric matrix 30.

Figure 3:
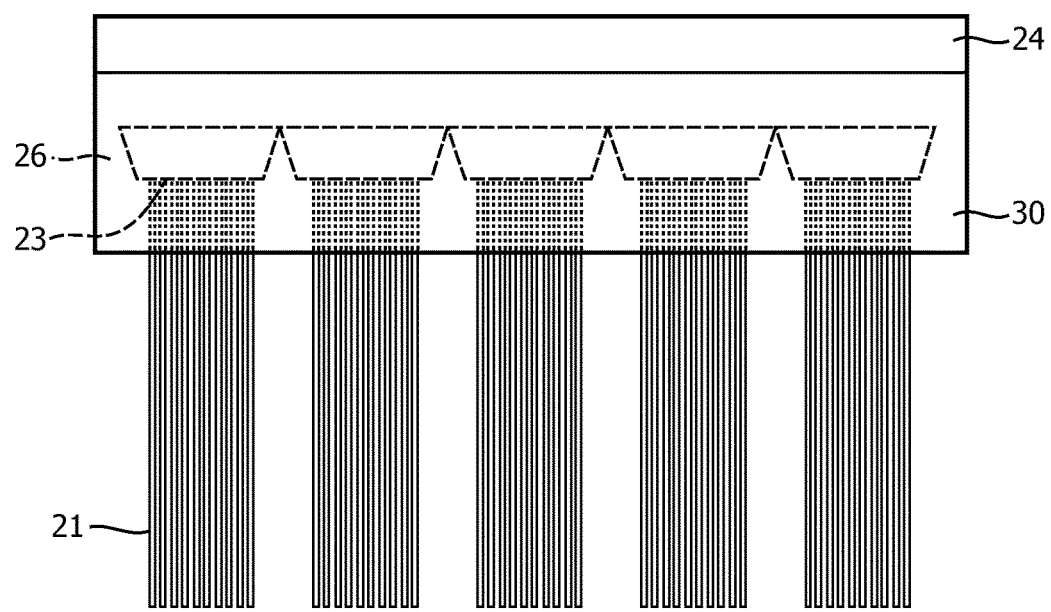
FIG. 3 is a schematic representation of a portion of a brush head assembly in accordance with an embodiment.

The proximal end head portion 26 can comprise a wide variety of different shapes and sizes. For example, the proximal end head portion 26 can be square, rounded, oval, triangular, trapezoidal, rectangular, u-shaped, or any of a wide variety of other shapes and sizes. Referring to FIG. 3, in one embodiment, is a cut-away view of a portion of the brush head 32. Each of the bristle tufts 21 has a proximal end 23 with a proximal end head portion 26 which is embedded in the elastomeric matrix 30. According to an embodiment, the proximal end head portions 26 of neighboring bristle tufts are joined during manufacture to form a network of bristle tufts which provides better adherence of the bristle tufts within the elastomeric matrix 30. In FIG. 3, for example, the proximal end head portions 26 are wedge-shaped or trapezoidal. The trapezoidal or wedge shape of the proximal end head portions further prevents the bristle tuft from being pulled out of or otherwise removed from the elastomeric matrix 30.

Figure 4:
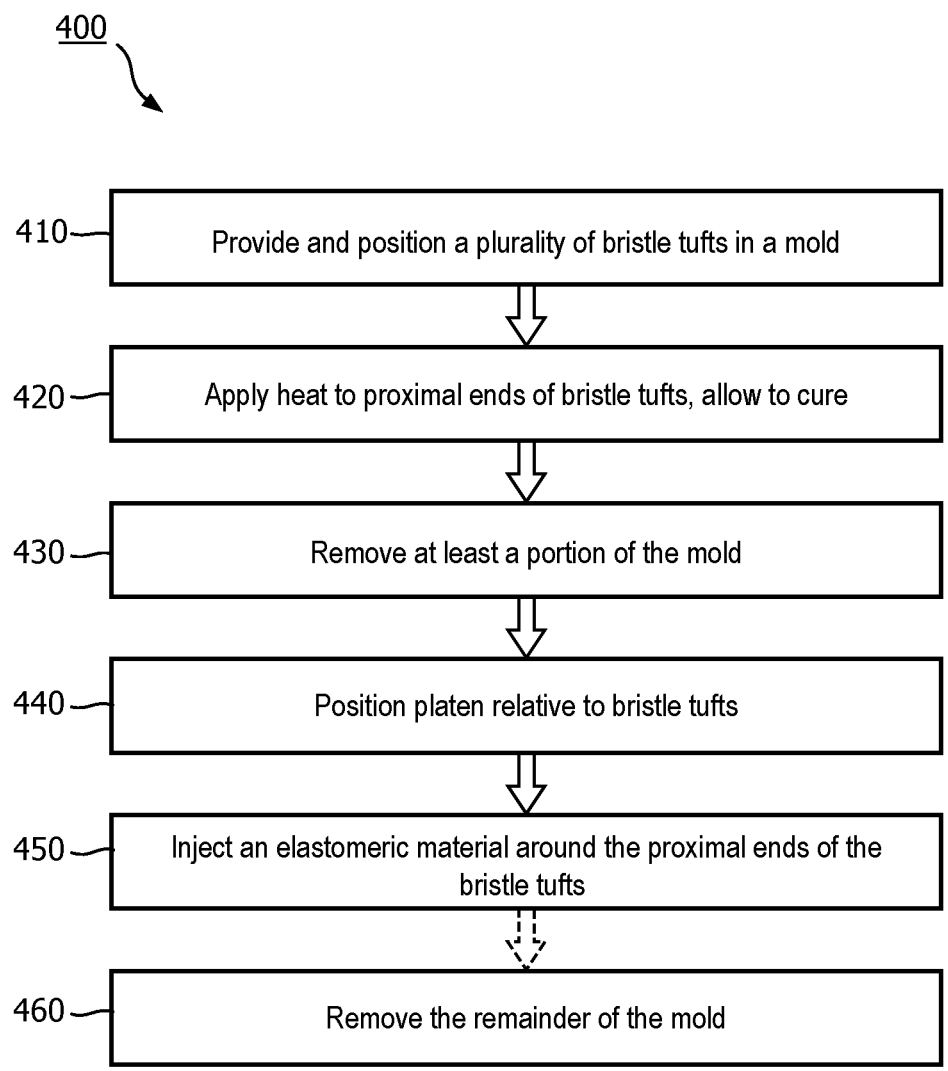
FIG. 4 is a flowchart of a method for manufacturing a brush head assembly with bristle tufts retained within an elastomeric matrix in accordance with an embodiment.

Referring to FIG. 4, in one embodiment, is a method 400 for manufacturing one or more of the various brush head embodiments and implementations described or otherwise envisioned herein. For example, brush head 32 can comprise a plurality of bristle tufts 21 each having a proximal end 23 and a free end 25, where the proximal end of each bristle tuft is retained within a flexible elastomeric matrix 30 to form a head portion 32 of the brush head assembly 100. According to an embodiment, the proximal end head portions 26 of the bristles are shaped to increase engagement with the elastomeric matrix 30, and/or to increase the force needed to remove the bristle tuft from the elastomeric matrix. Many other embodiments and configurations of the brush head 32 are possible.

Figure 5A:
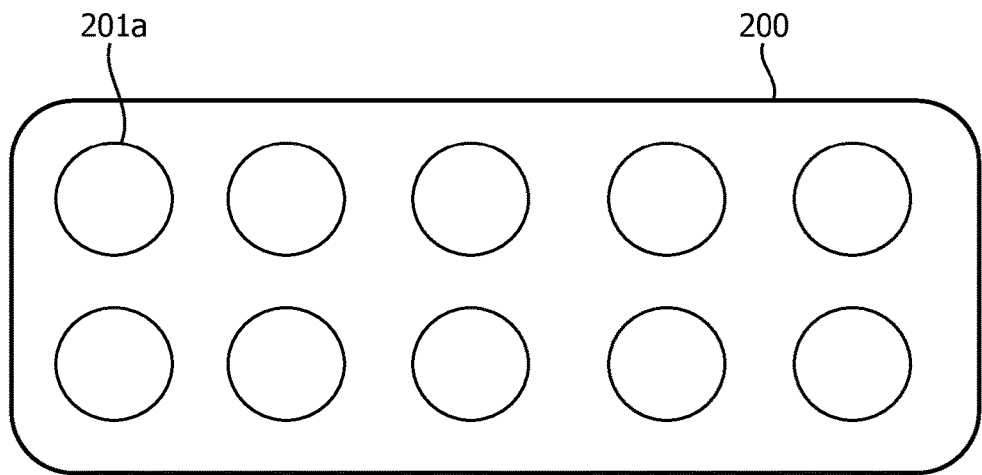
FIG. 5A is a schematic representation of a mold for a brush head assembly in accordance with an embodiment.
Figure 5B:
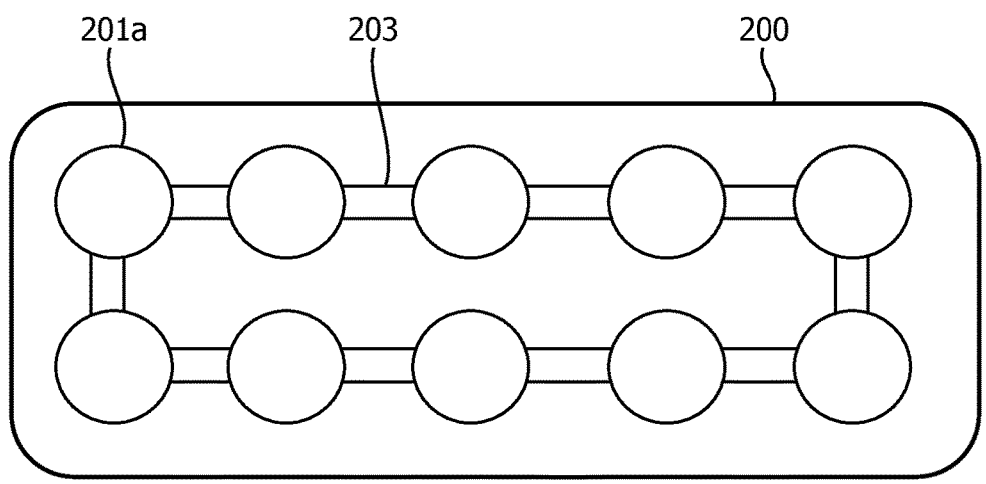
FIG. 5B is a schematic representation of a mold for a brush head assembly in accordance with an embodiment.

In step 410 of the method, a plurality of bristle tufts 21 each comprising a plurality of bristle strands is provided and positioned with respect to a mold having cavities 201*a* therethrough for holding and/or positioning the bristle tufts. Each bristle tuft includes a proximal end 23 and a free end 25, where the proximal end of each bristle tuft is retained within the brush head assembly 100. Referring to FIG. 5A, in one embodiment, is a die or mold 200. The mold 200 comprises a series of cavities 201*a* into which a bristle tuft can be inserted. In some embodiments, as shown in FIG. 5B, the cavities 201*a* can be connected to one or more neighboring or adjacent cavities by means of one or more channels 203. According to an embodiment, excess melt from the bristle tufts 21 can flow into and fill the channels when the hot knife or hot die is used to melt the bristle tufts, thereby interconnecting the bristle tufts to provide greater structure and increased retention of bristle tufts in the finished brush head.

Figure 6:
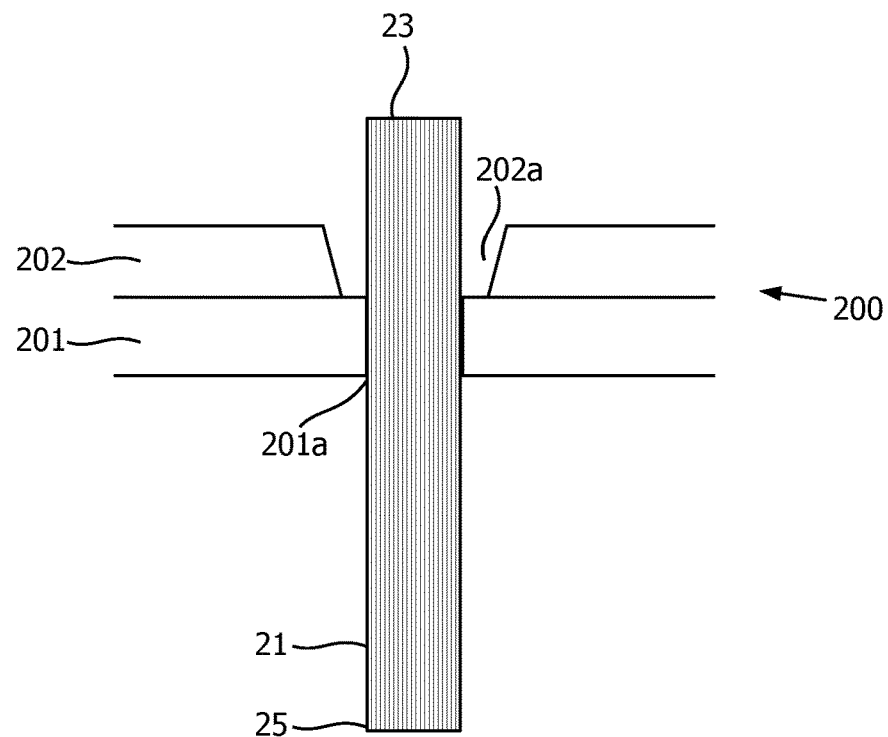
FIG. 6 is a schematic representation of a portion of a brush head during manufacturing in accordance with an embodiment.

Referring to FIG. 6, in one embodiment, is a cutaway side view of a bristle tuft 21 positioned within a cavity 201*a* of a mold 200. The mold comprises a top portion 202, a bottom portion 201, and cavity 201*a* sized and arranged to accept and hold the bristle tufts during manufacturing in the desired final brush head pattern. Proximal end 23 and free end 25 of the bristle tufts 21 project out both the top and bottom ends, respectively, of the openings 201*a* in the mold 200. The mold may have a top portion 202 adjacent to the proximal side of the top portion of the mold 201, that has cavities 202*a*, which are aligned with the openings 201*a* in the top portion of the mold 201, into which the proximal end 23 of the bristles extend.

Figure 7:
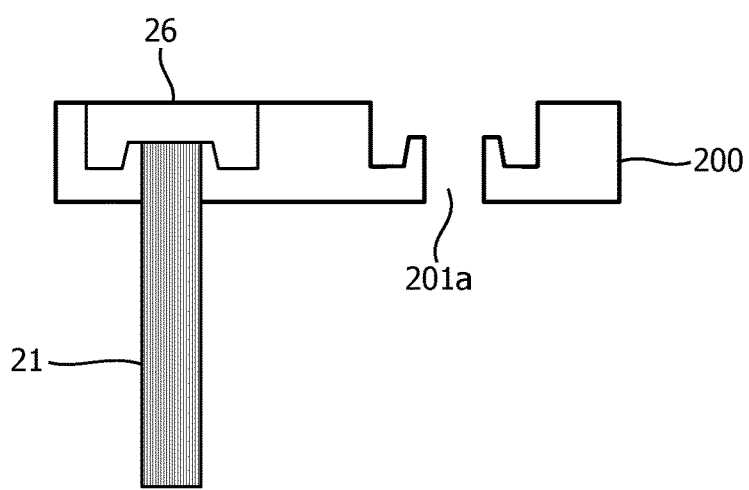
FIG. 7 is a schematic representation of a portion of a brush head assembly in accordance with an embodiment.

As shown in FIG. 7, the cavities 201*a* in the mold 200 can be a variety of shapes and sizes to provide for proximal end head portions 26 that will help to better secure the bristle tufts 21 in the elastomeric matrix 30. For example, in FIG. 7, the cavity is an inverted u-shaped cavity, and thus the proximal end head portion will adopt the u-shape when heated. The shape and size of the proximal end head portions 26 is important to help ensure the bristle tufts 21 are retained in the finished brush head during use. Additionally, if the elastomeric matrix is transparent or partially transparent, certain shapes for the proximal tuft end head portions 26 may provide better aesthetics for the finished product.

At step 420 of the method in FIG. 4, heat is applied to the proximal end 23 of the bristle tufts 21 to create a proximal end head portion 26 that is made by the melted material filling the cavities 202*a*. Accordingly, proximal end head portion 26 comprises the melted proximal end of the bristles in bristle tuft 21. The proximal end head portion 26 of the bristle tufts melt and form into the shape of the cavities in the mold. Additionally, in some arrangements, there are channels between the cavities in the mold, which also fill with melted bristle tuft material, or melted material smears across the top of the mold, and this additional melted material connects the bristle tuft head portions to each other.

Figure 8A:
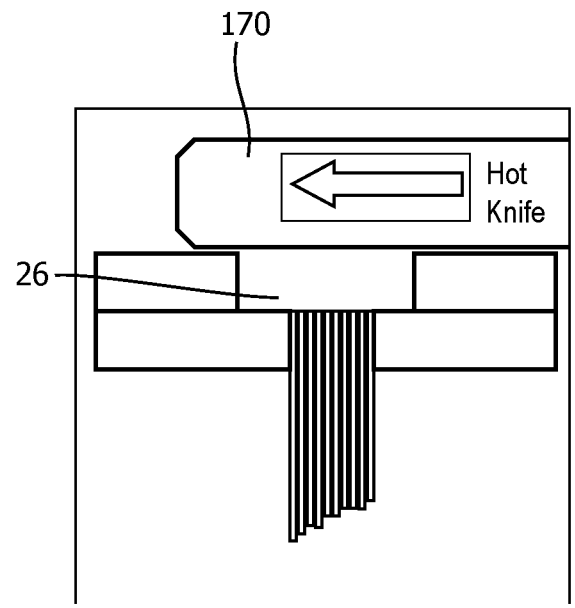
FIG. 8A is a schematic representation of a portion of a brush head assembly during manufacturing in accordance with an embodiment.
Figure 8B:
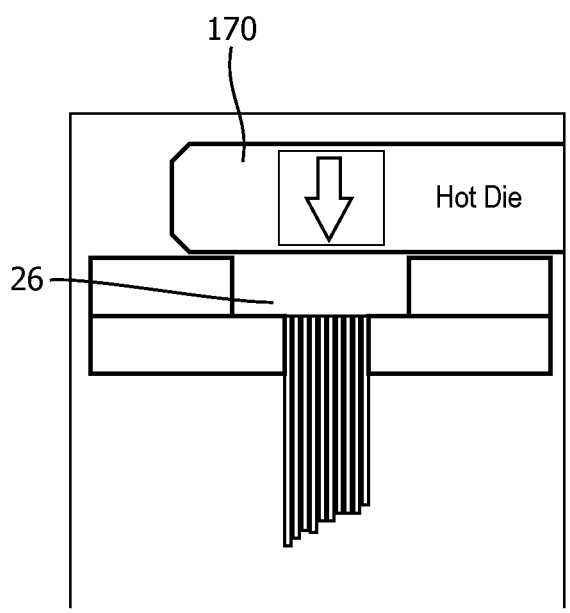
FIG. 8B is a schematic representation of a portion of a brush head assembly during manufacturing in accordance with an embodiment.

Referring to FIGS. 8A and 8B, the proximal ends 23 of the bristle tufts are heated to at least partially melt and fuse the bristles. The heat can be supplied by a heat source 170 that comes into direct physical contact with the proximal end 23 of the bristle tufts 21, such as a hot knife that moves across the top of the bottom mold 202 perpendicular to the bristle direction such as in FIG. 8A, a hot die that presses down onto the mold parallel to the bristle direction such as in FIG. 8B, or the heat can be supplied by heated air or any of a variety of other heat sources that come close to, but do not actually come into direct physical contact with the proximal end 23 of the bristle tufts 21. When heated, the melted portions of the proximal ends head portions 26 of the bristle tufts flow into and fill the cavities 202*a*.

At step 430 of the method in FIG. 4, at least a portion of the mold 200 is removed, or at least a portion of the plurality of bristle tufts is removed from the mold. Typically, this step is performed after the melted proximal end head portions 26 of the bristle tufts have cured, cooled, and/or hardened.

Figure 9A:
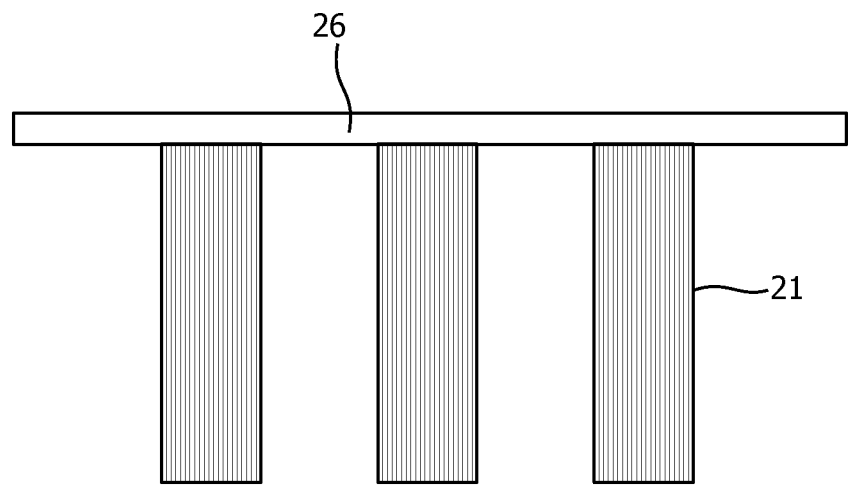
FIG. 9A is a schematic representation of a portion of a brush head assembly in accordance with an embodiment.
Figure 9B:
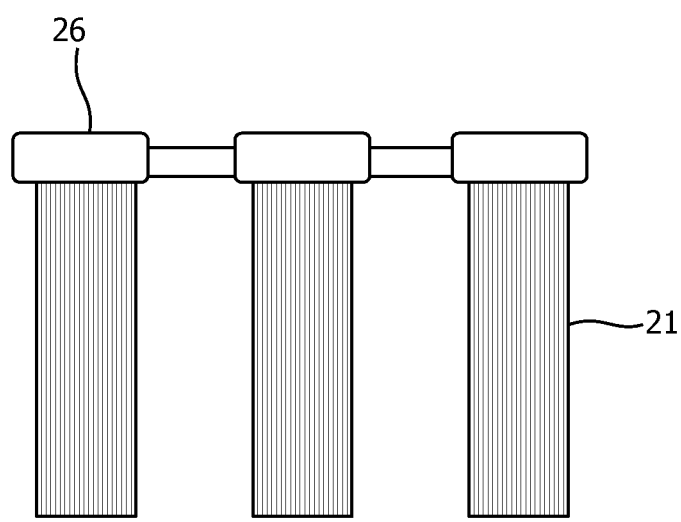
FIG. 9B is a schematic representation of a portion of a brush head assembly in accordance with an embodiment.

According to an embodiment, at least the bottom mold portion 202 is removed. In some arrangements, the top mold portion 201 is also removed, but in other arrangements, it stays in place during the next step of the manufacturing to help ensure bristle tuft positioning and arrangement until the brush head is completed. Referring to FIG. 9A, in one embodiment, after the melted bristle tufts have cooled and the mold is removed, the proximal end head portions 26 form an even or significantly even network for improved retention of the bristle tufts in the completed brush head. For example, the excess melted portion of the bristle tufts can be smeared or otherwise moved across the top of the mold by the movement of the hot knife and adjacent bristle tufts will be connected, forming a network. As shown in FIG. 9B, in one embodiment, the mold may comprise channels into which the melting proximal end of the bristle tufts can melt, thereby resulting in a slightly different interconnected network of proximal end head portions 26. After the material has cured, the interconnected network will remain in place after the mold is removed, providing greater structural strength and interconnection between bristle tufts, which will increase retention of bristle tufts in the finished brush head after the elastomeric matrix is molded around the components to form the finished brush head.

Figure 10:
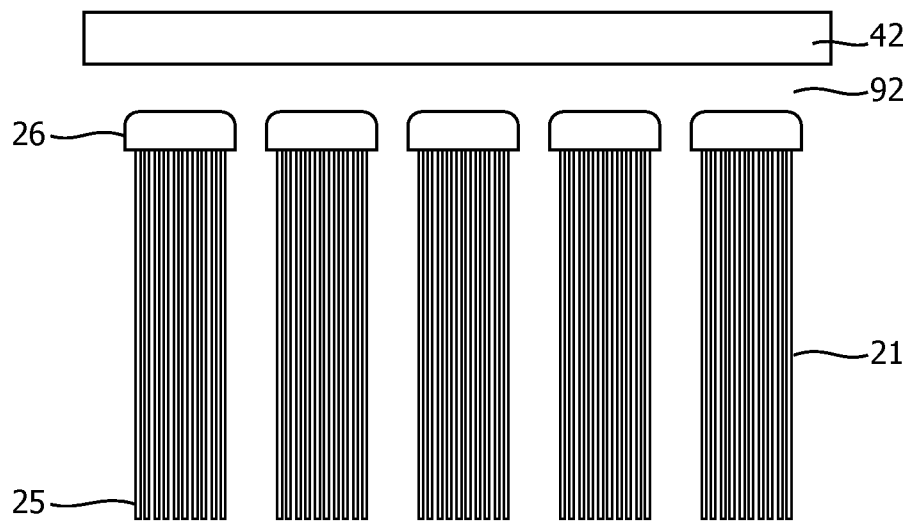
FIG. 10 is a schematic representation of a portion of a brush head assembly in accordance with an embodiment.

In step 440 of the method, the supporting portion 42 of the brush neck 40 is positioned in relation to the proximal end head portion 26 of the bristle tufts. Supporting portion of brush neck 42 can be properly positioned using a mold, for example, or other positioning mechanism. As shown in FIG. 10, in one embodiment, the supporting portion 42 of brush neck 40 is positioned above the bristle proximal end head portions. Again, depending on the arrangement, the supporting portion 42 of brush neck 40 can be directly adjacent to the proximal end head portions 26, or a space 92 can be left between the supporting portion of brush neck 42 and the proximal end head portion 26. According to an embodiment, the brush neck 40 can be designed to promote fusing of the elastomeric matrix to the brush neck. For example, if the brush neck is made from materials such as Spandex®, PolyMeg®, or similar copolymers, this would allow fusing of the elastomer matrix to the brush neck, thereby increasing retention forces. In addition, this design provides additional flexibility to the bristle tuft within the brush neck, and therefore additional degrees of freedom of motion within the brush head. However, many other materials and configurations for the brush neck 40 are possible.

In step 450 of the method in FIG. 4, an elastomeric material is molded over the at least a part of the supporting portion 42 of brush neck 40 and the head portion 26 of the bristle tufts to form an elastomeric matrix 30. According to an embodiment, elastomeric matrix 30 is preferably made from a flexible thermoplastic elastomer.

At optional step 460 of the method, after the elastomeric matrix 30 has cured/cooled/hardened, if the top portion 201 of the mold 200 was left in place, it can be removed. In some arrangements, the free end 25 of the bristle tufts 21 may be trimmed after manufacturing is completed.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for manufacturing a brush head, the method comprising the steps of:
   positioning a proximal end of each of a plurality of bristle tufts into a mold, the mold comprising a plurality of cavities each configured to receive at least one of the plurality of bristle tufts;
   applying heat to each of the bristle tuft proximal ends at a temperature and distance sufficient to at least partially melt the bristle tuft proximal end to create a proximal end head portion, wherein each of the cavities is further configured to at least partially shape the proximal end head portion as it at least partially melts;
   removing at least a portion of the mold, wherein removing the mold exposes the proximal end head portion of the plurality of bristle tufts; and
   molding a thermoplastic elastomer to create an elastomeric matrix that at least partially encompasses at least a portion of a supporting portion of a brush neck and the proximal end head portions.

2. The method of claim 1, further comprising the step of removing, after the molding step, a remaining portion of the mold.

3. The method of claim 1, further comprising the step of positioning a supporting portion of brush neck in proximity to the proximal end head portions.

4. The method of claim 1, wherein the mold further comprises one or more channels between at least some of the cavities, wherein the channels are configured to receive at least a portion of a melted bristle tuft during the applying step.

5. The method of claim 1, wherein at least a portion of each of the cavities of the mold comprises a trapezoidal shape.

6. The method of claim 1, wherein at least a portion of each of the cavities of the mold comprises u-shape.

7. The method of claim 1, wherein the proximal end head portions of two or more neighboring bristle tufts are interconnected.

* * * * *